United States Patent
Ishii

(10) Patent No.: US 8,383,745 B2
(45) Date of Patent: Feb. 26, 2013

(54) METHOD FOR PRODUCING N-METHYL-N-VINYLACETAMIDE HAVING IMPROVED STABILITY AND POLYMERIZABILITY

(75) Inventor: Tetsuya Ishii, Tokyo (JP)

(73) Assignee: Showa Denko K.K., Tokyo (JP)

( * ) Notice: Subject to any disclaimer, the term of this patent is extended or adjusted under 35 U.S.C. 154(b) by 364 days.

(21) Appl. No.: 12/810,466

(22) PCT Filed: Dec. 24, 2008

(86) PCT No.: PCT/JP2008/073371
§ 371 (c)(1),
(2), (4) Date: Jun. 24, 2010

(87) PCT Pub. No.: WO2009/084520
PCT Pub. Date: Jul. 9, 2009

(65) Prior Publication Data
US 2010/0280204 A1   Nov. 4, 2010

(30) Foreign Application Priority Data
Dec. 27, 2007 (JP) ................................. 2007-335408

(51) Int. Cl.
*C07C 233/09* (2006.01)
*C08F 20/54* (2006.01)

(52) U.S. Cl. ..................................... 526/307.1; 564/215
(58) Field of Classification Search ................ 526/307.1
See application file for complete search history.

(56) References Cited

U.S. PATENT DOCUMENTS

| 5,641,881 A | 6/1997 | Ruhl et al. |
| 5,789,619 A | 8/1998 | Aizawa et al. |
| 6,072,084 A * | 6/2000 | Aizawa et al. ............... 564/215 |
| 2006/0287548 A1 | 12/2006 | Hoefer et al. |

FOREIGN PATENT DOCUMENTS

| JP | 8-59584 A | 3/1996 |
| JP | 8-81428 A | 3/1996 |
| JP | 2007-533624 A | 11/2007 |

* cited by examiner

Primary Examiner — Vu A Nguyen
(74) Attorney, Agent, or Firm — Sughrue Mion, PLLC

(57) ABSTRACT

The present invention relates to a method for producing N-methyl-N-vinylacetamide, which comprises a step for controlling the N-1,3-butadienyl-N-methylacetamide content in N-methyl-N-vinylacetamide to 0.01-150 ppm. This method enables production of N-methyl-N-vinylacetamide having a stable quality, which can be controlled in stability and polymerizability as a monomer. N-methyl-N-vinylacetamide produced by the method enables production of an N-methyl-N-vinylacetamide polymer having stable physical properties such as a molecular weight.

6 Claims, No Drawings

US 8,383,745 B2

METHOD FOR PRODUCING N-METHYL-N-VINYLACETAMIDE HAVING IMPROVED STABILITY AND POLYMERIZABILITY

TECHNICAL FIELD

The present invention relates to a polymerization inhibitor which improves stability and/or polymerizability of N-methyl-N-vinylacetamide, a method for producing N-methyl-N-vinylacetamide containing the polymerization inhibitor in a specific amount, and a polymer made by polymerizing N-methyl-N-vinylacetamide obtained by the production method.

Specifically, the present invention relates to a method for producing N-methyl-N-vinylacetamide having improved stability and/or polymerizability, comprising controlling the content of N-1,3-butadienyl-N-methylacetamide in a specific range, which N-1,3-butadienyl-N-methylacetamide has polymerization inhibitory effect and stabilizing effect on N-methyl-N-vinylacetamide and enables controlling the polymerization of the same, which N-methyl-N-vinylacetamide is an industrially useful monomer used for producing N-methyl-N-vinylacetamide-based polymer that is useful for contact lenses, thickners for oil drilling, gas hydrate inhibitors, coating agents, bio-based materials, a base for drug delivery systems, a base for cosmetics, lubricant additives for fuels, a coagulant, a liquid absorbent, a thicker and the like; a homopolymer made by polymerizing N-methyl-N-vinylacetamide obtained by the production method; and a copolylmer obtained by copolymerizing N-methyl-N-vinylacetamide and other monomers.

BACKGROUND ART

A number of methods for producing N-methyl-N-vinylacetamide have been proposed to date. For example, a method of reacting vinyl acetate and N-methylacetamide in the presence of base such as dimethyl aminopyridine and the like have been disclosed (Patent Document 1: JP-A-H08-59584; U.S. Pat. No. 5,641,881). However, these methods do not disclose a substance inhibiting polymerization of N-methyl-N-vinylacetamide.

On the other hand, a radical scavenger having at least two glycine units has been proposed as a polymerization stabilizer of N-vinylacetamide compounds (Patent Document 2: JP-A-2007-533624; U.S. patent publication No. 2006/287548). However, these scavengers need to be synthesized separately to be added to the compound and furthermore may have an adverse affect such as coloring on the polymer if the scavengers remained in the polymer after polymerization.

Also, a method for producing highly polymerizable N-vinyl carboxylic acid amide (Patent Document 3: JP-A-H08-81428) has been disclosed. However, the invention relates to highly polymerizable N-vinyl carboxylic acid amide, high molecular weight polymer produced thereof and purifying treatment of N-vinyl carboxylic acid amide, and does not disclose polymerization inhibition, stabilization and polymerization control.

N-methyl-N-vinylacetamide is used as an intermediate and a material for industrial chemicals such as surfactant, a reactive diluent, and medicines. Since N-methyl-N-vinylacetamide is liquid at ordinary temperatures, it is at risk for starting polymerization during storage and transportation. Once polymerization occurs, it is impossible to stop it, which may cause a significant accident. But Patent Document 3 does not disclose the stability of the monomer.

N-methyl-N-vinylacetamde homopolymer and copolymer (N-methyl-N-vinylacetamide-based polymer) can be obtained by polymerizing N-methyl-N-vinylacetamide only or by copolymerizing it with other monomers. These polymers can be used for contact lenses, thickners for oil drilling, gas hydrate inhibitors, coating agents, bio-based materials, a base for drug delivery systems, a base for cosmetics, lubricant additives for fuels, a coagulant, a liquid absorbent, a thickner and the like. However, since the polymerizability of material monomers is not the same among the production lots, there has been a problem of difficulty in obtaining polymers having desired physical properties such as molecular weight and concentration of residual monomers.

[Patent Document 1] JP-A-H08-59584
[Patent Document 2] JP-A-2007-533624
[Patent Document 3] JP-A-H08-81428

DISCLOSURE OF THE INVENTION

Problems to be Solved by the Invention

An objective of the present invention is to provide a method for producing stabilized N-methyl-N-vinylacetamide having reproducible polymerizability by controlling the concentration of a specific compound which has inhibitory effect and stabilizing effect on N-methyl-N-vinylacetamide and enables controlling the polymerizability of N-methyl-N-vinylacetamide within a specific range.

Another objective of the present invention is to provide a method for producing N-methyl-N-vinylacetamide-based polymers having stable quality and being made by polymerizing N-methyl-N-vinylacetamide only or copolymerizing it with other monomers, which N-methyl-N-vinylacetamide is obtained by the above-mentioned method.

Means to Solve the Problem

The present inventors have made a study to solve the above-mentioned problem and found that adding a polymerization inhibitor such as phenothiazine and hydroquinone leads to expression of unexpected decrease in polymerization and remarkable degradation of the properties of the obtained polymer, which may cause difference in polymerizability among production lots. As a result of intensive studies based on the finding, the present inventors have found that N-1,3-butadienyl-N-methylacetamide has a polymerization inhibitory effect, stabilizing effect and polymerization controlling effect on N-methyl-N-vinylacetamide. That is, the present inventors have found that N-1,3-butadienyl-N-methylacetamide in N-methyl-N-vinylacetamide serves as a polymerization inhibitor; and the polymerization inhibitory effect, stabilizing effect and polymerization controlling effect are seen to thereby obtain N-methyl-N-vinylacetamide being excellent in stability and polymerizability of a monomer by controlling the content of N-1,3-butadienyl-N-methylacetamide to 0.01 to 150 ppm, preferably 0.05 to 100 ppm, more preferably 0.1 to 30 ppm; and have accomplished the present invention. In the present specification and claims, ppm indicates mass ppm.

That is, the present invention relates to the method for producing N-methyl-N-vinyl acetamide; homopolymer and copolymer of N-methyl-N-vinyl acetamide produced by the method and a production method of the homopolymer and copolymer; N-methyl-N-vinylacetamide having improved stability and polymerizability; a method for stabilizing N-methyl-N-vinylacetamide; and a polymerization inhibitor and an agent for improving stability and polymerizability of N-methyl-N-vinylacetamide as follows.
1. A method for producing N-methyl-N-vinylacetamide, comprising a step of controlling the content of N-1,3-butadienyl-N-methylamide in N-methyl-N-vinylacetamide to 0.01 to 150 ppm.
2. A method for producing N-methyl-N-vinylacetamide having improved stability and/or polimerizability, comprising a step of controlling the content of N-1,3-butadienyl-N-methylamide in N-methyl-N-vinylacetamide to 0.01 to 150 ppm.
3. The method for producing N-methyl-N-vinylacetamide as described in 1 or 2 above, which N-methyl-N-vinylacetamide is obtained by methylating N-vinylacetamide.
4. The method for producing N-methyl-N-vinylacetamide as described in 1 or 2 above, which N-methyl-N-vinylacetamide is obtained by thermally decomposing N-methyl-N-(1-alkoxyethyl)acetamide.
5. The method for producing N-methyl-N-vinylacetamide as described in any one of 1 to 4 above, wherein the method for controlling the content of N-1,3-butadienyl-N-methylacetamide in N-methyl-N-vinylacetamide is the treatment by a precision distillation method of N-methyl-N-vinylacetamide or a solution thereof, a physical absorption method by activated carbon absorber, Diels-Alder reaction method or a selective hydrogenation reaction method of 1,3-butadienyl group.
6. The method for producing N-methyl-N-vinylacetamide as described in 3 above, wherein N-vinylacetamide is methylated using halogenated methyl.
7. The method for producing N-methyl-N-vinylacetamide as described in 3 or 6 above, wherein tetrahydrofuran is used as a solvent in the above-mentioned methylation reaction of N-methyl-N-vinylacetamide.
8. The method for producing N-methyl-N-vinylacetamide as described in 1 or 2 above, wherein the content of N-1,3-butadienyl-N-methylacetamide is controlled to 0.05 to 100 ppm.
9. The method for producing N-methyl-N-vinylacetamide as described in 8 above, wherein the content of N-1,3-butadienyl-N-methylacetamide is controlled to 0.1 to 30 ppm.
10. A method for producing N-methyl-N-vinylacetamide homopolymer, comprising polymerization of N-methyl-N-vinylacetamide produced by a method described in any one of 1 to 9 above.
11. A method for producing N-methyl-N-vinylacetamide copolymer, comprising copolymerization of N-methyl-N-vinylacetamide produced by a method described in any one of 1 to 9 above and other copolymerizable monomers.
12. An N-methyl-N-vinylacetamide homopolymer for contact lenses produced by the method as described in 10 above.
13. An N-methyl-N-vinylacetamide copolymer for contact lenses produced by the method as described in 11 above.
14. N-methyl-N-vinylacetamide having improved stability and/or polymerizability containing N-1,3-butadienyl-N-methylacetamide having polymerization inhibitory effect on N-methyl-N-vinylacetamide in an amount of 0.01 to 150 ppm.
15. A method for stabilizing N-methyl-N-vinylacetamide, comprising controlling the content of N-1,3-butadienyl-N-methylacetamide in N-methyl-N-vinylacetamide to 0.01 to 150 ppm.
16. A polymerization inhibitor of N-methyl-N-vinylacetamide, which is composed of N-1,3-butadienyl-N-methylacetamide.
17. An agent for improving stability and/or polymerizability of N-methyl-N-vinylacetamide, which is composed of N-1,3-butadienyl-N-methylacetamide.

EFFECTS OF THE INVENTION

The present invention enables inhibiting polymerization, stabilizing and controlling polymerization of N-methyl-N-vinylacetamide easily. Specifically, N-methyl-N-vinylacetamide having stability and stable polymerizability as a monomer can be obtained by controlling the content (concentration) of N-1,3-butadienyl-N-methylacetamide serving as a polymerization inhibitor of N-methyl-N-vinylacetamide to 0.01 to 150 ppm.

Also, N-methyl-N-vinylacetamide-based polymer having a stable quality can be produced by using N-methyl-N-vinylacetamide obtained by the method of the present invention.

BEST MODE FOR CARRYING OUT THE INVENTION

Hereinafter, the present invention is described in more details.

N-methyl-N-vinylacetamide used in the present invention is represented by the following formula (I):
[Chem. 1]

$$CH_2=CH-N(CH_3)-COCH_3 \qquad (I)$$

N-1,3-butadienyl-N-acetamide used in the present invention is represented by the following formula (II):
[Chem. 2]

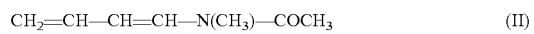

$$CH_2=CH-CH=CH-N(CH_3)-COCH_3 \qquad (II)$$

and exsists as two geometric isomers of a cis-isomer and a trans-isomer. N-1,3-butadienyl-N-acetamide in the present invention means both of the isomers.

In the present invention, N-methyl-N-vinylacetamide having stable polymerizability can be obtained by controlling the content of N-1,3-butadienyl-N-methylacetamide in N-methyl-N-vinylacetamide to 0.01 to 150 ppm. Desired polymerization stability can be obtained by controlling the content to preferably 0.05 to 100 ppm, more preferably 0.1 to 30 ppm. When the content is less than 0.01 ppm, it poses a risk for starting polymerization during storage and transportation. When the content is more than 150 ppm, it will reduce polymerizability.

There are no particular limitations on the method for producing N-methyl-N-vinylacetemide of the present invention as long as the method allows to obtain N-methyl-N-vinylacetamide having the N-1,3-butadienyl-N-methylacetamide content of 0.01 to 150 ppm.

In order to control the N-1,3-butadienyl-N-methylacetamide content in N-methyl-N-vinylacetamide to 0.01 to 150 ppm to thereby produce N-methyl-N-vinylacetamide having stable polymerizabitily by in the present invention, the following treatment methods can be used: i.e. a treatment method of reducing the content by removing N-1,3-butadienyl-N-methlacetamide contained in excess in N-methyl-N-vinylacetamide during the production process or adding N-1,3-ubtadienyl-N-methylacetamide to compensate for the shortfall in N-methyl-N-vinylacetamide; and a treatment method of reducing the content of N-1,3-butadienyl-N-methylacetamide or its precursor by removing these contained in excess in the material or intermediate of N-methyl-N-vinylacetamide or adding N-1,3-butadienyl-N-methylacetamide or its precursor to compensate for the shortfall in the material or intermediate of N-methyl-N-vinylacetamide. An appropriate analysis method such as liquid chromatography is available for determining quantity of the content of N-1,3-butadienyl-N-methylacetamide or its precursor in N-methyl-N-vinylacetamide or the material or intermediate thereof to decide whether the content of these is in excess or deficient relative to a desired content.

Generally, it is often the case that N-1,3-butadienyl-N-methylacetamide is generated during the synthesis or purification of N-methyl-N-vinylacetamide and thus removing the excess of N-1,3-butadienyl-N-methylacetamide is required to thereby reduce the content. Therefore, generally it is not necessary to add N-1,3-butadienyl-N-methylacetamide separately.

First, the method of reducing the N-1,3-butadienyl-N-methylacetamide content by removing the excess of N-1,3-butadieny-N-methylacetamide in N-methyl-N-vinylacetamide is described below.

Examples of an embodiment of the treatment of removing the excess of N-1,3-butadienyl-N-methylacetamide in N-methyl-N-vinylacetamide to thereby reduce the content include physical treatment methods such as a precision distillation method of N-methyl-N-vinylacetamide or a solution thereof and a treatment method using an absorber such as activated carbon; and treatment methods of chemically converting N-1,3-butadienyl-N-methylacetamide such as a treatment method by Diels-Alder reaction with p-benzoquinone and the like and a treatment method of 1,3-butathenyl group by selective hydrogenation reaction. These methods can be used singly or in combination of two or more of them. The treatment method is not particularly limited to the methods exemplified above as long as the method can easily isolate an excess of N-1,3-butadienyl-N-methylacetamide in N-methyl-N-vinylacetamide or can chemically convert an excess of N-1,3-butadienyl-N-methylacetamide.

Hereinafter, the method of reducing the N-1,3-butadienyl-N-methylacetamide content by removing an excess of N-1,3-butadieny-N-methylacetamide in N-methyl-N-vinylacetamide is described in more details.

In the method of the present invention, there are no particular limitations on the distillation apparatus in the case where an excess of N-1,3-butadienyl-N-methylacetamide in N-methyl-N-vinylacetamide by precision distillation to thereby reduce the content, and a tray column and a packed bed having the number of theoretical trays of 1 to 50 are used, and it is desirable to use a distillation column having a low pressure loss and high rectifying efficiency. Examples of such a column include a packed column with structured packings. Since N-methyl-N-vinylacetamide is liable to thermal alteration, it is desirable to perform distillation at as low a temperature as is possible. Thus, distillation is generally performed under reduced pressure of 0.01 to 100 mmHg. Though the precision distillation can be performed either in a continuous way or in a discontinuous way, continuous distillation is preferable from the viewpoint of productivity and operation stability. There are no particular limitations on the reflux ratio and configured depending on the N-1,3-butadienyl-N-methylacetamide content, performance of the distillation column. However, the reflux ratio of about 0.1 to 20 is generally satisfactory, and the ratio is preferably 0.5 to 10.

In the case where the N-1,3-butadienyl-N-methylacetamide content is reduced by isolating N-1,3-butadienyl-N-methylacetamide contained in excess in N-methyl-N-vinylacetamide or a solution thereof by subjecting them to the treatment using an adsorbent such as activated carbon in the present invention, there are no particular limitations on the adsorbent as long as it is capable of selectively adsorbing N-1,3-butadienyl-methylacetamide compared to N-methyl-N-vinylacetamide. Examples of adsorbents include activated carbon, clays, alumina, silica, zeolite and absorptive resin such as ion-exchange resin. Among these, activated carbon is preferable.

When carrying out the adsorption operation, N-methyl-N-vinylacetamide or its solution may be directly in contact with an adsorbent. When N-methyl-N-vinylacetamide is made into a solution, N-methyl-N-vinylacetamide is dissolved in a solvent which is not reactive with N-methyl-N-vinylacetamide and has appropriate solubility and brought into contact with the adsorbent. Examples of such a solvent include aromatic hydrocarbon such as benzene, toluene and xylene; aliphatic hydrocarbon such as pentane, cyclopentane, hexane, cyclohexane and heptane; alcohol such as methanol, ethanol, n-propyl alcohol, isopropyl alcohol, n-butanol, isobutanol, sec-butanol, t-butanol and cyclohexanol; halogenated hydrocarbon such as methylene chloride, chloroform and chlorobenzene; ketones such as acetone, methylethylketone and cyclohexanone; esters such as methyl acetate, ethyl acetate, propyl acetate and butyl acetate; ethers such as diethyl ether and dimethoxyethane; amides such as N,N-dimethylformamide and N,N-dimethylacetamide; dimethyl sulfoxide; and water. Particularly, toluene, cyclohexane, methanol, isopropyl alcohol and water are preferable. When activated carbon is used as an adsorbent, water and methanol are particularly preferable as a solvent. There are no particular limitations on the ratio of the solvent and N-methyl-N-vinylacetamide. When water and methanol are used as a solvent, it is desirable to make the ratio of the solvent ten times N-methyl-N-vinylacetamide or less, preferably within the range of 0.1 to three times by mass. Though an optimal temperature for carrying out the adsorption operation depends on the type of the absorbent, a temperature of from −20° C. to 100° C., particularly from 0° C. to 80° C., is preferable. If the temperature is lower than −20° C., the diffusion of the adsorbent into the pores will be remarkably retarded, thereby prolonging the adsorption time period. When the temperature is higher than 100° C., adsorption equilibrium remarkably decreases as well as the stability of N-methyl-N-vinylacetamide.

The adsorption method may be carried out in either of a batch mode and a continuous mode and there are no severe limitations on the structural style.

In the present invention, the N-1,3-butadienyl-N-methylacetamide content in N-methyl-N-vinylacetamide may be controlled to 0.01 to 150 ppm by chemically treating N-methyl-N-vinylacetamide or a solution thereof. There are no particular limitations on the chemical reaction to be used, but a reaction using the difference in reactivity between N-methyl-N-vinylacetamide and N-1,3-butadienyl-N-methyl acetamide: i.e. a reaction which is highly active with N-1,3-butadienyl-N-methylacetamide and inactive with N-methyl-N-vinylacetamide, is particularly preferable.

Hereinafter, a method of subjecting N-methyl-N-vinylacetamide or a solution thereof to the treatment by Diels-Alder reaction and a method of subjecting N-methyl-N-vinylacetamide or a solution thereof to selective hydrogenation treatment are described below as a representative example. When N-methyl-N-vinylacetamide or a solution thereof is subjected to the treatment by Diels-Alder reaction, the treatment is carried out by making dienophile of the Diels-Alder reaction coexist with N-methyl-N-vinylacetamide or a solution thereof. There are no particular limitations on dienophile as long as the compound is generally known as a dienophile in the Diels-Alder reaction: i.e. a compound among unsaturated compounds substituted by an electron-withdrawing group, which is not reactive with N-methyl-N-vinylacetamide. Examples of dienophile include unsaturated carboxylic acid esters such as acrylic acid ester, maleic acid ester and fumaric acid ester; unsaturated ketones such as methyl vinyl ketone and p-benzoquinone; unsaturated nitriles such as acrylonitrile; and unsaturated imides such as maleic acid imide. Among these, p-benzoquinone is particularly preferable. There are no particular limitations on the amount of these compounds as long as the amount is equivalent to or more than N-1,3-butadienyl-N-methylacetamide contained in N-methyl-N-acetamide or a solution thereof. Generally, the compound is used in an amount of 1 to 100 times equivalent, preferably 1.2 to 10 times equivalent to N-1,3-butadienyl-N-methylacetamide contained in N-methyl-N-vinylacetamide or a solution thereof by molar ratio. Here, it is preferable to use dienophile in such an amount that the N-1,3-butadienyl-N-methylacetamide content in N-methyl-N-vinyl-acetamide after the treatment becomes the upper limit of 150 ppm or less. Also, if a dienophile is used in such an amount that the N-1,3-butadienyl-N-methylacetamide becomes the lower limit of 0.01 ppm or more, it eliminates the need to add the deficit of N-1,3-butadienyl-N-methylacetamide later.

When N-methyl-N-vinylacetamide is made into a solution and subjected to the treatment by Diels-Alder reaction, N-methyl-N-vinylacetamide is subjected to Diels-Alder reaction after being dissolved in a solvent which is not reactive with N-methyl-N-vinylacetamide and has appropriate solubility. Examples of such a solvent include those exemplified in the above-mentioned treatment method by adsorption. When N-methyl-N-vinylacetamide or a solution thereof is subjected to the treatment by Diels-Alder reaction, generally there is no need for using a catalyst but a catalyst which is generally said to have a catalytic activity in Diels-Alder reaction and unreactive with N-methyl-N-vinylacetamide may be used. Examples of such a catalyst include Lewis acids such as aluminum trichloride, boron trifluoride and lanthanide complex. The optimal reaction temperature for carrying out Diels-Alder reaction depends on the type of dienophile to be used but a temperature of from −20° C. to 100° C., particularly from 0° C. to 80° C., is preferable. If the temperature is lower than −20° C., the reaction is remarkably retarded, which is undesirable. When the temperature is higher than 100° C., the stability of N-methyl-N-vinylacetamide is reduced, which is undesirable. N-methyl-N-vinylacetamide or a solution thereof subjected to the treatment by Diels-Alder reaction contains Diels-Alder adducts generated by Diels-Alder reaction, which has almost no inhibitory effect on the polymerization of N-methyl-N-vinylacetamide. Furthermore, the Diels-Alder adducts generated in the present invention has a lower vapor pressure compared to N-1,3-butadienyl-N-methylacetamide. Accordingly, when N-methyl-N-vinylacetamide or a solution thereof is subjected to the treatment by Diels-Alder reaction of the present invention and then distilled, an excess of N-1,3-butadienyl-N-methylacetamide can be isolated more easily compared to the case where it is removed by distillation only. That is, an excess of N-1,3-butadienyl-N-methylacetamide as a Diels-Alder adduct can be isolated with a simpler equipment.

In the present invention, examples of the treatment method by subjecting N-methyl-N-vinylacetamide or a solution thereof to selective hydrogenation include a method to be carried out by making N-methyl-N-vinylacetamide or a solution thereof, water and a catalyst coexist. There are no particular limitations on the catalyst as long as it is generally active in the selective hydrogenation but it is desirable that the catalyst exhibits high selectivity in hydrogenation of dienes in the coexistence with monoolefin and diene. Examples of the catalyst includes metal such as Pd-based metal, Co—Mo-based metal and Ni—Co—Cr-based metal or a catalyst modified by these metals (metal complex) supported on alumina, activated carbon and silica. Particularly, alumina-based catalysts such as a Pd-alumina catalyst, Pd—Ag-alumina catalyst, Pd—Pb-alumina catalyst and Pd—Cr-alumina catalyst are preferable. When Pd is used as a metal component, the Pd loading is preferably 0.001 to 5 mass %, more preferably 0.01 to 1 mass % to the support (alumina and the like). When the loading is less than 0.001 mass %, the reaction is remarkably retarded, which is undesirable. When the loading is more than 5 mass %, N-methyl-N-ethylacetamide which is produced by adding hydrogen to N-methyl-N-vinylacetamide increases, which is undesirable.

When N-methyl-N-vinylacetamide is subjected to the treatment by hydrogenation reaction, N-methyl-N-vinylacetamide may be brought into contact directly with hydrogen and a catalyst or may be subjected to hydrogenation reaction after being dissolved in a solvent having appropriate solubility. Examples of such a solvent include those exemplified in the above-mentioned treatment method by adsorption. Among these, alcohol is preferable and methanol and isopropyl alcohol are particularly preferable. These solvents may be used singly or in combination of the two or more thereof.

An optimal temperature for carrying out hydrogenation reaction depends on the type of the solvent to be used, but a temperature of from −20° C. to 100° C., particularly from 0° C. to 80° C., is preferable. If the temperature is lower than −20° C., the reaction is remarkably retarded, which is undesirable. When the temperature is higher than 100° C., the stability of N-methyl-N-vinylacetamide is reduced, which is undesirable.

An optimal hydrogen partial pressure for carrying out selective hydrogenation is 0.98 to 9800 kPa, preferably 49 to 4900 kPa. When the hydrogen partial pressure is lower than 0.98 kPa, the reaction is remarkably retarded, which is undesirable. When the pressure is higher than 9800 kPa, hydrogen is added to N-methyl-N-vinylacetamide, thereby increasing production of N-methyl-N-ethylacetamide and resulting in a high equipment cost, which is undesirable. When a catalyst is packed to allow N-methyl-N-vinylacetamide to flow through the catalyst, appropriate conditions for the liquid-space velocity depend on hydrogen partial pressure, reaction temperature and N-1,3-butadienyl-N-methylacetamide content but 0.05 to 1000 [$Hr^{-1}$] is preferable. When the liquid-space velocity exceeds 1000, it fails to achieve sufficient N-1,3-butadienyl-N-methylacetamide conversion and is undesirable. When the liquid-space velocity is less than 0.05, it will reduce reaction efficiency, which is undesirable.

The hydrogenation reaction may be carried out in either of a batch mode and a continuous mode and there are no severe limitations on the structural style. Either of gas-solid contact, gas-liquid contact and solid-liquid contact is available but a solid-liquid reactor is preferable, which enables bringing the raw material into uniform contact with the catalyst under relatively mild conditions. When the solid-liquid reaction is carried out, hydrogen required for the reaction is to be supplied by dissolving hydrogen in N-methyl-N-vinylacetamide or a solution thereof in advance. The reaction solution after hydrogenation reaction contains by-product during the production and a product generated by hydrogenation reaction.

There are no particular limitations on the method for isolating the product and by-product by processing the reaction solution as long as N-methyl-N-vinylacetamide can be easily isolated from the product and by-product. Examples of the method include precision distillation of the reaction liquid and treatment using an adsorbent such as activated carbon. These methods can be used singly or in combination. As discussed above, since N-1,3-butadienyl-N-methylacetamide exists as a cis-isomer and a trans-isomer, the difference in physical properties and reactivity between the isomers may result in difference in the degree of isolation. In such case, the degree of isolation may be controlled by combining the cis-trans isomerization reaction of N-1,3-butadienyl-N-methylacetamide under appropriate reaction conditions with the above-discussed operation for isolation.

In each case, N-methyl-N-vinylacetamide causes solvolysis or hydrolysis reaction in the presence of acid. Accordingly, it is desirable to locate the production equipment, isolation equipment and accompanying equipment such as a material tank, product containers and a filtrate tank in atmosphere such as nitrogen and dry air. Also, a small amount of desiccant such as magnesium sulfate may be added to the material in order to prevent hydrolysis reaction of N-methyl-N-vinylacetamide. Furthermore, N-methyl-N-vinylacetamide causes dimerization reaction in the presence of base. Accordingly, it is desirable to adjust the pH of N-methyl-N-vinylacetamide or a solution thereof at from 5 to 10, which is in a weak acid to weak alkaline region, preferably from 6 to 9, still more preferably from 7 to 8, which is in a neutral to weak alkaline region, before carrying out the operation of distillation and adsorption. In the case of adjusting the pH of acid N-methyl-N-vinylacetamide or a solution thereof, the adjustment is carried out by adding basic compounds.

Examples of the basic compounds include sodium salts such as sodium carbonate, sodium hydrogen carbonate, sodium hydroxide, sodium (hydrogen) phosphate and sodium acetate; potassium salts such as potassium carbonate, potassium hydrogen carbonate, potassium hydroxide, potassium (hydrogen) phosphate and potassium acetate; aromatic amines such as N-phenyl-α-naphthylamine, 4,4'-bis(α,α-dimethylbenzyl)diphenylamine, N-phenyl-N'-(1,3-dimethylbutyl)-p-phenylenediamine, N-phenyl-N'-isopropyl-p-phenylenediamine, N-phenyl-N'-(1-methylheptyl)-p-phenylenediamine, N-phenyl-N'-cyclohexyl-p-phenylenediamine, N,N'-diphenyl-p-phenylenediamin, N,N'-di-3-naphthyl-p-phenylenediamine, N,N'-bis(1-ethyl-3-methylpentyl)-p-phenylenediamine, N,N'-bis(1-methylheptyl)-p-phenylenediamine and N-phenyl-N'-(p-toluenesulfonyl)-p-phenylenediamine. Among these, sodium hydrogen carbonate is particularly preferable.

The additive amount of the basic compound is preferably from 1 ppm to 10,000 ppm, particularly preferably from 10 ppm to 1,000 ppm. If a basic compound is added in an amount more than 10,000 ppm, it cannot be fully dissolved in the case where the basic compound is an inorganic salt, and effects based on the additive amount cannot be eventually expected. Also, it becomes difficult to completely remove the basic compound during the purification process when the basic compound is aliphatic amines, which rather decreases polymerizability of N-methyl-N-vinylacetamide. When a basic compound is added in an amount of less than 1 ppm, it has little effect as a stabilizer.

In the case of adjusting the pH of a basic solution of N-methyl-N-vinylacetamide, the adjustment is carried out by adding acidic compounds. Examples of the acidic compounds includes inorganic acidic compounds such as hydrochloric acid, sulfuric acid, nitric acid, phosphoric acid and salts thereof; and organic acidic compounds: e.g. carboxylic acids such as acetic acid, phthalic acid and citric acid, carbolic acids such as phenol, hydroquinone and catechol.

Next, the method of reducing the content of N-1,3-butadienyl-N-methylacetamide or its precursor by isolating an excess thereof contained in the material or intermediate of N-methyl-N-vinylacetamide is described. Here, the precursor content in the material or intermediate is expressed by an amount corresponding to the amount of N-1,3-butadienyl-N-methylacetamide generated by converting the total amount of the above precursor in the material or intermediate.

In the method of the present invention, examples of a material or an intermediate of N-methyl-N-vinylacetamide include N-(1-alkoxyethyl)-N-methylacetamide, acetaldehyde dialkyl acetal and ethylidene bis acetamide. Examples of the alkoxyl group of N-(1-alkoxyethyl)-N-methylacetamide and acetaldehyde dehydrodialkyl acetal include aliphatic alkoxyl groups such as methoxy group, ethoxy group, n-propoxy group, isopropoxy group, n-butoxy group and sec-butoxy group. Examples of the acetamide group of N-(1-alkoxyethyl)-N-methylacetamide and ethylidene bis acetamide include N-methylacetamide group. As the compound corresponding to the group, examples of N-(1-alkoxyethyl) carboxylic amide include N-(1-methoxyethyl)-N-methylacetamide, N-(1-ethoxyethyl)-N-methylacetamide and N-(1-isopropxyethyl)-N-methylacetamide; examples of acetaldehyde dialkyl acetal include dimethyl acetal, diethyl acetal and diisopropoxy acetal; and examples of ethylidene bis acetamide include ethylidene bis N-methylacetamide.

The conversion of these N-(1-alkoxyethyl)-N-methylacetamide and ethylidene bis-N-methylacetamide to N-methyl-N-vinylacetamide is carried out by a known method such as thermal decomposition and catalytic cracking. Examples of the reaction conditions include a gas-phase or liquid phase method, reaction temperature of from 60 to 600° C., reaction time of from 0.3 second to two hours, and reaction pressure of from 0.1 mmHg to atmospheric pressure. A catalytic cracking may be carried out with or without a catalyst. Examples of the catalyst to be used include alkaline metal salts of carboxylic acids such as potassium acetate and an oxide of alkaline metal or alkaline earth metal such as potassium oxide and magnesium oxide.

N-1,3-butadienyl-N-methylacetamide is to be generated by elimination reaction in the presence of two equivalents of alcohol through thermal decomposition or catalytic crashing of N-methyl-N-(1,3-dialkoxybutyl)acetamide; or by elimination reaction of alcohol and N-methylacetamide through thermal decomposition or catalytic cracking of 3-alkoxybutylidene bis-N-methylacetamide.

N-(1,3-dialkoxybutyl)-N-methylacetamide and 3-alkoxybutylidene bis N-methylacetamide are generated by a reaction of 1,1,3-trialkoxybutane and N-methylacetamide and the like.

Accordingly, examples of the precursors of N-1,3-butadienyl-N-methyl-acetamide in the present invention include 1,1,3-trialkoxybutane, N-(1,3-dialkoxybutyl)-N-methylacetamide and 3-alkoxybutylidene bis N-methylacetamide; and examples of the alkoxy group of the precursor thereof include those exemplified above as the alkoxy group of a material or a intermediate of N-methyl-N-vinylacetamide. Examples of 1,1,3-trialkoxybutane include 1,1,3-trimethoxybutane, 1,1,3-triethoxybutane and 1,1,3-triisopropoxybutane; and examples of N-(1,3-dialkoxybutyl)-N-methylacetamide include N-(1,3-dimethoxybutyl)-N-methylacetamide, N-(1,3-diethooxybutyl)-N-methylacetamide and N-(1,3-diisopropoxybutyl)-N-methylacetamide; and examples of 3-alkoxybutylidene bis N-methylacetamide include 3-methoxybutylidene bis N-methylacetamide, 3-ethoxybutylidene bis N-methylacetamide and 3-isopropoxybutylidene bis N-methylacetamide.

When N-1,3-butadienyl-N-methylacetamide or its precursor is added to compensate for the shortfall in N-methyl-N-vinylacetamide, N-1,3-butadienyl-N-methylacetamide may be added as it is or in the form of a solution using solvent. Examples of the solvents include aromatic hydrocarbon such as benzene, toluene and xylene; aliphatic hydrocarbon such as pentane, cyclopentane, hexane, cyclohexane and heptane; alcohols such as methanol, ethanol, n-propyl alcohol, isopropyl alcohol, n-butanol, isobtanol, sec-butanol, t-butanol and cyclohexanol; halogenated hydrocarbon such as methylene chloride, chloroform and chlorobenzene; ketones such as acetone, methylethyl ketone and cyclohexanone; esters such as methyl acetate, ethyl acetate, propyl acetate and butyl acetate; ethers such as diethyl ether and dimethoxy ethane; amides such as N,N-dimethylformamide and N,N-dimethylacetamide; dimethylsulfoxide; etc. These may be used singly or in a mixture of two or more thereof. Particularly preferred are toluene, cyclohexane, methanol and isopropyl alcohol.

Examples of a method for producing N-methyl-N-vinylacetamide include a method of synthesizing vinyl acetate and N-methylacetamide using palladium-based catalysts and a method of synthesizing by thermally degrading N-methyl-N-(1-alkoxyethyl)acetamide. The most preferable method is a method of reacting N-vinylacetamide using a methylating agent such as halogenated methyl in the presence of base to thereby obtain N-methyl-N-vinylacetamide. The method enables stable production as well as high yield. For N-vinylacetamide serving as a material, "NVA monomer" (registered trademark) manufactured by Showa Denko K. K. is preferable due to high polimerizability. Examples of halogenated methyl include methyl chloride, methyl iodide and methyl bromide, and methyl iodide is preferable from the viewpoint of reactivity. When the reaction is conducted using methyl chloride, the reactivity can be improved by adding potassium iodide.

There are no particular limitations on a reaction solution and examples include tetrahydrofuran (THF), 1,4-dioxane, diethyl ether, dimethoxyethane, diethylene glycol dimethyl ether, benzene, toluene, xylene, hexamethylphosphoric triamide, N,N-dimethylformamide, N,N-dimethylacetamide, dimethyl sulfoxide, liquid ammonia, triethylamine, pyrimidine and 1,3-dimethylimidazolidinone; and THF is particularly preferable. These may be used singly or in a mixture of two or more thereof. There are no particular limitations on a base to be used for the reaction, and examples thereof include sodium hydrogen carbonate, potassium hydrogen carbonate, sodium carbonate, potassium carbonate, butyllithium, potassium t-butoxide, sodium methoxide, sodium ethoxide, potassium methoxide, potassium ethoxide, sodium hydride, potassium hydride, sodium amide, potassium amide, lithium diisopropylamide, potassium diisopropylamide, lithium diethylamide, lithium isopropylcyclohexylamide, lithium-2,2,6,6-tetramethylpiperidine, isopropyl ethylamine, pyridine, triethyl amine, N,N,N',N'-(N,N-dimethylamino)pyridine, diisopropyl amine, benzyl methylamine, 2,6-di-t-butylpyridine, 2,6-di-t-butyl-4-methylpyridine, 2,6-lutidine and 1,8-diaminonaphthalene. Potassium t-butoxde is particularly preferable.

Examples of an embodiment to control the content of N-1, 3-butadienyl-N-methylacetamide or its precursor in a material or an intermediate of N-methyl-N-vinylacetamide to a target level of from 0.01 to 150 ppm include a precision distillation method, recrystallization method by cooling a solution of the precursor of N-methyl-N-vinylacetamide, pressure crystallization of the same solution, physical adsorption by subjecting the same solution to the treatment using an adsorbent such as activated carbon, and a method of subjecting the same solution to chemical treatment. These methods can be used singly or in combination thereof. Also, other than the methods exemplified above, there are no particular limitations on a method as long as a method is capable of easily isolating an excess of N-1,3-butadienyl-N-methylacetamide or its precursor from the material or intermediate of N-methyl-N-vinylacetamide. As mentioned above, it is often the case that N-1,3-butadienyl-N-methylacetamide is generated during the synthesis or purification of N-methyl-N-vinylacetamide and generally, the content of N-1,3-butadienyl-N-methylacetamide is reduced by removing an excess thereof. However, if necessary, N-1,3-butadienyl-N-methylacetamide or its precursor which falls short of a target level may be added to a material or an intermediate of N-methyl-N-vinylacetamide at this stage.

The use of a N-methyl-N-vinylacetamide polymer, wherein the N-1,3-butadienyl-N-methylacetamide content in N-methyl-N-vinylacetamide is 0.01 to 150 ppm, enables production of N-methyl-N-vinylacetamide homopolylmers or copolymers with other polymerizable monomers with good reproducibility.

In the present invention, examples of monomers which is copolymerizable with N-methyl-N-vinylacetamide include the following: acrylic acid, methacrylic acid (hereinafter to be collectively referred to as "(meth)acrylic acid") or alkali metal salts thereof such as sodium salts and potassium salts; alkyl ester thereof such as methyl ester, ethyl ester, propyl ester, butyl ester, pentyl ester, hexyl ester, heptyl ester, octyl ester, nonyl ester, decyl ester, stearyl ester and palmityl ester; hydroxy lower alcohol thereof such as hydroxyethyl ester, hydroxypropyl ester and hydroxybutyl ester; lower alkyl ester substituted with lower alkyl amino group such as dimethylaminomethyl ester, dimethylaminoethyl ester, dimethylaminopropyl ester, dimethylaminobutyl ester, diethylaminomethyl ester, diethylaminoethyl ester, diethylaminopropyl ester and diethylaminomethyl ester; lower alkyl ester halide (which halide is preferably chloride or bromide) substituted with quaternary ammonium group such as trimethylammoniumethylester halide, trimethylammoniopropylester halide, triethylammonioethylester halide and triethylammoniopropylester halide; amides thereof; amides substituted with lower alkyl amino group such as dimethylaminomethyl amide, dimethylaminoethyl amide, dimethylaminopropyl amide, dimethylaminobutyl amide, diethylaminomethyl amide, diethylaminoethyl amide, diethylaminopropyl amide and diethylaminobutyl amide; lower alkyl amide substituted with quaternary ammonium group such as trimethylammoniumethylamide halide, triethylammoniumethylemide halide and triethylammoniumpropylamide halide; lower alkyl amide substituted with sulfonic acid or alkali metal sulfonate such as sulfo methyl amide, sulfo ethyl amide, sulfo propyl amide, sulfo butyl amide, sodium sulfo methyl amide, sodium sulfo ethyl amide, potassium sulfo methyl amide, potassium sulfo ethyl amide, potassium sulfo propyl amide and potassium sulfo butyl amide;

silicone-based macromer and perfluoro modified macromer thereof, silicone-based macromer such as polyalkylene glycol modified macromer, poly siloxane macromer such as bifunctional organic siloxane (II), α,ω-bis(3-(meth)acryloxypropylmethylsiloxy)3,3,3-trifluoropropyl-methylpolysiloxane, α,ω-bis(3-(meth)acryloxypropyl)tetrakis(trimethylsiloxy)silyl 3,3,3-trifluoropropylmethylpolysiloxane, α,ω-bis(2-(meth)acryloxypropyldimethylsiloxy)3,3,3-trifluoropropylmethylpolysiloxane, (meth)acrylate substituted with isocyanate such as (meth)acryloxyethyl isocyanate and (meth)acryloyl isocyanate;

isocyanate compounds containing acrylate group or methacrylate group obtained by reacting hydroxy group-containing acrylate or hydroxy group-containing methacrylate such as hydroxyethyl(meth)acrylate and hydroxybutyl(meth)acrylate with various diisocyanate compounds;

silicone-based monomer such as tris(trimethylsiloxy)silylpropyl(meth)acrylate, bis(trimethylsiloxy)methylsilylpropyl(meth)acrylate, pentamethyldisiloxanepropyl(meth)acrylate, tris(trimethylsiloxy)silylpropyloxyethyl(meth)acrylate and tris(polydimethylsiloxy)silylpropyl(meth)acrylate; hydrophilic siloxanyl(meth)acrylate in which a urethane bond or hydrophilic group such as glyceryl group and polyalkylene glycol group exists between siloxanyl group and (meth)acrylate group, or in which a part of siloxanyl group is substituted with terminal hydroxy group or polyalkylene glycol group;

fluorosilicone-based monomer such as tris(dimethyltrifluoropropylsiloxy)silylpropyl(meth)acrylate;

perfluoroalkyl-based monomer such as 2,2,2-trifluoroethyl (meth)acrylate, 2,2,3,3,3-pentafluoropropyl(meth)acrylate and hexafluoroisopropyl(meth)acrylate;

fluoroalkyl-based or fluoroalkylether-based monomer containing hydroxy group such as 1,1,2,2-tetrafluoroethoxy-2-hydroxypropyl(meth)acrylate; ethyleneglycoldi(meth)acrylate, tetraethyleneglycoldi(meth)acrylate, tetramethyldisiloxanebis(propyl(meth)acrylate);

acrylonitrile; vinyl ether such as methyl vinyl ether, ethyl vinyl ether, propyl vinyl ether and butyl vinyl ether; vinyl ketone such as methyl vinyl ketone and ethyl vinyl ketone; lower carboxylic acid vinyl such as vinyl acetate and vinyl propanoate; maleic anhydride, maleic acid, sodium malate and potassium malate.

Among these, particularly preferred are (meth)acrylic acid, sodium (meth)acrylate, methyl (meth)acrylate, ethyl(meth)acrylate, propyl (meth)acrylate, butyl(meth)acrylate, 2-hydroxyethyl (meth)acrylate, 2-hydroxypropyl(meth)acrylate, 2-hydroxybutyl(meth)acrylate, dimethylaminoethyl (meth)acrylate, trimethylaminoethyl(meth)acrylate chloride, acrylamide, sulfopropyl acrylamide, sodium sulfobutyl acrylamide, acrylonitrile, methyl vinyl ether, ethyl vinyl ether, methyl vinyl ketone, ethyl vinyl ketone, vinyl acetate, N-vinyl-2-pyrrolidone, N-vinyl acetamide, N-methyl-N-methylformamide, N-vinylformamide and maleic anhydride.

As a monomer copolymerizable with N-methyl-N-vinylacetamide, a crosslinkable monomer having at least two saturated groups in a molecule or a crosslinking agent may be used in the present invention. There are no particular limitations on the polymerization method and conventionally known methods may be used. Generally, polymerization by solution polymerization, reversed phase suspension polymerization, reversed phase emulsion polymerization and the like is preferable. For example, as a solution polymerization method, after dissolving a monomer component and a crosslinking agent uniformly in a solvent such as water, an organic solvent or a mixture thereof; and removing dissolved oxygen in a system by vacuum deaeration or replacement with inert gas such as nitrogen and carbon dioxide; reaction is conducted by the addition of a polymerization initiator. Generally, the polymerization initiation temperature is about −10 to 60° C., and the reaction time is about one to ten hours.

In the present invention, there are no particular limitations on the method for determining quantity of N-1,3-butadienyl-N-methylacetamide but the determination by high-performance liquid chromatography is preferable. For example, the following measurement conditions of high-performance liquid chromatography are preferable. In the present invention, quantity of N-1,3-butadienyl-N-methylacetamide was determined under these conditions unless otherwise noted.

Column: SHODEX 5SIL-4B

Eluent: n-hexane/isopropyl alcohol=9/1

Flow rate: 1 ml/min.

Detector: ultoraviolet photodetector 254 nm

EXAMPLES

Hereinafter, the present invention will be explained in more detail below with reference to Manufacturing Examples, Examples and Comparative Examples, but the present invention is not limited thereto.

Manufacturing Example 1

7.31 g (0.1 mol) of N-methylacetamide, 21.47 g (0.67 mol) of methanol, 2.16 g (15 mmol) of ethylidene bis(N-methylacetaqmide), 9.01 g (0.1 mol) of acetaldehyde dimethyl acetal were put in a three neck flask (200 ml) provided with a thermometer and a trap cooled with dry ice-ethanol, stirred and dissolved at 45 to 48° C. to be made into a uniform solution. After a solution of 0.04 g of concentrated sulfuric acid (0.1 mass % to the amount of the above charged materials) dissolved in 1.06 g (33 mmol) of isopropyl alcohol was added and stirred, 17.62 g (0.4 mol) of acetaldehyde was added thereto through a dropping funnel over three minutes. After the dropping is completed, the reaction was performed at 50° C. for three hours and the determination by gas chromatography after the neutralization of the catalyst showed N-methylacetamide conversion of 86%, selectivity of 93% for N-(1-methoxyethyl)-N-methylacetamide and selectivity of 5.2% for ethylidene bis(N-methylacetamide) as a by-product. From the obtained reaction solution, N-(1-methoxyethyl)-N-methylacetamide was obtained and thermally decomposed into N-methyl-N-vinylacetamide and methanol by reduced-pressure distillation at 450° C. in a residence time of one second. The pyrolysis liquid was cooled to 20° C. and distilled at 20 mmHg and 65° C., thereby obtaining N-methyl-N-vinylacetamide having purity of 99.8% and N-1,3-butadienyl-N-methylacetamide content of 810 ppm.

To evaluate the polymerizability of N-methyl-N-vinylacetamide obtained in the above Manufacturing Example 1, 25 g of N-methyl-N-vinylacetemide was added to 25 g of distilled water and subjected to nitrogen substitution, and then 20.0 mg of 2,2'-Azobis(2-amidinopropane dihycrochloride (V-50; manufactured by Wako Pure Chemical Industries, Ltd.) was added and the resultant solution was dipped in a constant-temperature bath of 70° C. After 30 minutes, the solution was diluted by adding 150 g of an aqueous solution of 1% hydroquinone. The diluted solution was measured using a BL-type viscometer at 20° C. and 300 rpm and found to have a viscosity of 10 mPa·s or less.

Example 1

The pyrolysis liquid obtained in Manufacturing Example 1 was distilled under the following conditions. Glass beads were packed in a 20 mm×500 mm distillation column and treated at the reflux ratio of 0.3 (specified number of plates: about ten plates). 50 ml each of Fractions 1 to 7 and the residue were isolated from the first boiling at 63° C. (21 mmHg). Next, Fractions 2 and 3 were mixed and subjected to simple distillation to obtain N-methyl-N-vinylacetamide having purity of 97.5% and the N-1,3-butadienyl-N-methylacetamide content of 146 ppm. The test of evaluating polylmerizability performed in the same way as in Manufacturing Example 1 and the result showed that N-methyl-N-vinylacetamide had viscosity of 130 mPa·s.

Example 2

245 g of potassium t-butoxide was added to a mixed solution of 150 g of N-vinylacetamide manufactured by SHOWA DENKO K.K. and 2680 g of THF (potassium t-butoxide/N-vinylacetamide=1.2 (molar ratio)). Next, 302 g of methyl iodide (99.5%) was added thereto and stirred (methyl iodide/

N-vinylacetamide=1.2 (molar ratio)). The mixed slurry solution was filtrated through filter paper (5C) and the filtrate was condensed using an evaporator (40° C.). Subsequently, the filtrate was distilled at 20 mmHg and 65° C., thereby obtaining N-methyl-N-vinylacetamide having purity of 98% (total yield: 69%). The obtained N-methyl-N-vinylacetamide was clear and colorless liquid having the N-1,3-butadienyl-N-methylacetamide concentration of 30 ppm. The test of evaluating polylmerizability performed in the same way as in Manufacturing Example 1 and the result showed that N-methyl-N-vinylacetamide had viscosity of 160 mPa·s.

Comparative Example 1

4-dimethylaminopyridine was added as a catalyst to a mixture of vinyl acetate (1 mol) and N-methylacetamide (1 mol) and reacted at 60° C. Next, the mixture was distilled at 12 mmHg and 85° C. to thereby obtain N-methyl-N-vinylacetamide having purity of 96% (total yield: 72%). The obtained N-methyl-N-vinylacetamide was liquid tinged with light brown having a N-1,3-butadienyl-N-methylacetamide concentration of 760 ppm. The test of evaluating polylmerizability performed in the same way as in Manufacturing Example 1 and the result showed that N-methyl-N-vinylacetamide had viscosity of 10 mPa·s or less.

Example 3

5 g of solid catalyst in which 0.5 mass % of palladium was supported on an alumina support and mixed liquid containing N-1,3-butadienyl-N-methylacetamide in 810 ppm, 55 mass % of N-methyl-N-vinylacetamide, 15 mass % of N-methyl-N-(1-methoxyethyl)acetamide, 7 mass % of N-methylacetamide and 20 mass % of methanol were put in a 200 ml-volume flask and reacted under hydrogen atmosphere at normal temperature while being stirred for 30 minutes.

After completion of the reaction, the catalyst was filtrated from the reaction liquid and the filtrate was analyzed. N-1,3-butadienyl-N-methylacetamide was subjected to the analysis by high performance liquid column chromatography manufactured by Shimadzu Corporation and the other components were subjected to the analysis by gas chromatography GC-17A manufactured by Shimadzu Corporation.
Carrier gas: nitrogen
Column: DB-WAX ID: 0.25 mm, Film: 0.25 μm, length: 30 m
Flow rate: 0.9 ml/min.
Split ratio: 60
Column temperature: maintained at 40° C. for seven minutes, heated to 150° C. at a rate of 25° C./min. and maintained for 15 minutes, and heated to 220° C. at a rate of 25° C./min. and maintained for 22 minutes
Injection temperature: 200° C.
Detector: FID
Detector temperature: 220° C.
N-1,3-butadienyl-N-methylacetamide and N-ethyl-N-methylacetamide were contained in 0.5 ppm and 0.4 mass % respectively in the reaction liquid. N-methyl-N-vinylacetamide obtained after removing methanol by distillation under reduced pressure had purity of 99.1 mass % and the N-1,3-butadienyl-N-methylacetamide content of 0.2 ppm. The test of evaluating polylmerizability performed in the same way as in Manufacturing Example 1 and the result showed that N-methyl-N-vinylacetamide had viscosity of 240 mPa·s or less.

The polymerization of N-methyl-N-vinylacetamide obtained by reaction between vinyl acetate and N-methylacetamide or degradation reaction of ethylidene bis(N-methylacetamide) obtained as an intermediate from N-methylacetamide, acetaldehyde and alcohol, or acetaldehyde and N-methylacetamide, which are conventional method for producing N-methyl-N-vinylacetamide, showed low reproducibility. However, a method which comprises controlling the N-1,3-butadienyl-N-methylacetamide content in the N-methyl-N-vinylacetamide to 0.01 to 150 ppm, preferably 0.05 to 100 ppm, more preferably 0.1 to 30 ppm enabled production of N-methyl-N-vinylacetamide which was improved in polymerizability. Also, use of the above N-methyl-N-vinylacetamide enabled production of N-methyl-N-vinylacetamide-based polymer having a stable quality.

A method of obtaining N-methyl-N-vinylacetamide by reacting N-vinylacetamide using a methylating agent such as halogenated methyl enabled stable production with high yield. The method enabled controlling the N-1,3-butadieyl-N-methylacetamide content (concentration) in N-methyl-N-vinylacetamide within the range of from 0.01 to 150 ppm by simple distillation after the reaction. Also, the method enabled producing high-quality N-methyl-N-vinylacetamide free of coloration stably in good yields.

Industrial Applicability

The present invention enables producing N-methyl-N-vinylacetamide having improved stability and/or polymerizability by controlling the N-1,3-butadienyl-N-methyacetamide content in N-methyl-N-vinylacetamide within a specific range, which N-methyl-N-vinylacetamide is an industrially useful monomer used for producing N-methyl-N-vinylacetamide-based polymer that is useful for contact lenses, thickners for oil drilling, gas hydrate inhibitors, coating agents, bio-based materials, a base for drug delivery systems, a base for cosmetics, lubricant additives for fuels, a coagulant, a liquid absorbent, a thickner and the like. Specifically, controlling the N-1,3-butadienyl-N-methyacetamide content in N-methyl-N-vinylacetamide to 0.01 to 150 ppm, which N-1,3-butadienyl-N-methyacetamide serves as a polymerization inhibitor of N-methyl-N-vinylacetamide, enables inhibiting unintended polymerization and thereby obtaining N-metthyl-N-vinylacetamide-based polymers having a stable quality.

The invention claimed is:

1. A method for producing N-methyl-N-vinylacetamide, comprising a step of controlling the content of N-1,3-butadienyl-N-methylacetamide in N-methyl-N-vinylacetamide to 0.01 to 150 ppm,
   which N-methyl-N-vinylacetamide is obtained by methylating N-vinylacetamide.

2. The method for producing N-methyl-N-vinylacetamide as claimed in claim 1, wherein the method for controlling the content of N-1,3-butadienyl-N-methylacetamide in N-methyl-N-vinylacetamide is the treatment by a precision distillation method of N-methyl-N-vinylacetamide or a solution thereof, a physical absorption method by activated carbon absorber, Diels-Alder reaction method or a selective hydrogenation reaction method of 1,3-butadienyl group.

3. The method for producing N-methyl-N-vinylacetamide as claimed in claim 1, wherein N-vinylacetamide is methylated using halogenated methyl.

4. The method for producing N-methyl-N-vinylacetamide as claimed in claim 1, wherein tetrahydrofuran is used as a solvent in the methylation reaction of N-methyl-N-vinylacetamide.

5. A method for producing N-methyl-N-vinylacetamide homopolymer, comprising polymerization of N-methyl-N-vinylacetamide produced by a method claimed in claim 1.

6. A method for producing N-methyl-N-vinylacetamide copolymer, comprising copolymerization of N-methyl-N-vinylacetamide produced by a method claimed in claim 1 and other copolymerizable monomers.

* * * * *